(12) United States Patent
Rustad et al.

(10) Patent No.: US 7,721,734 B2
(45) Date of Patent: May 25, 2010

(54) INHALATION APPARATUS

(75) Inventors: Andre Rustad, Etiwanda, CA (US); Rob Simas, Keene, NH (US)

(73) Assignee: Carefusion 2200, Inc., San Diego, CA (US)

( * ) Notice: Subject to any disclaimer, the term of this patent is extended or adjusted under 35 U.S.C. 154(b) by 461 days.

(21) Appl. No.: 10/846,415

(22) Filed: May 14, 2004

(65) Prior Publication Data

US 2005/0252509 A1    Nov. 17, 2005

(51) Int. Cl.
*A61M 15/00* (2006.01)
*A61M 16/10* (2006.01)
*A61M 11/00* (2006.01)
*A61M 16/00* (2006.01)
*A62B 7/00* (2006.01)

(52) U.S. Cl. .......................... 128/203.12; 128/200.14; 128/204.18

(58) Field of Classification Search ............ 128/200.14, 128/200.18, 202.22, 203.12, 203.23, 203.25, 128/200.23, 200.24, 911–912, 200.21, 204.18, 128/204.26, 203.24; 604/256
See application file for complete search history.

(56) References Cited

U.S. PATENT DOCUMENTS

| | | | |
|---|---|---|---|
| 322,908 A * | 7/1885 | Corbly ........................ 239/403 |
| 3,826,255 A * | 7/1974 | Haystad et al. ......... 128/200.18 |
| 4,007,238 A | 2/1977 | Glenn |
| 4,119,105 A | 10/1978 | Owens, Jr. |
| 4,655,212 A | 4/1987 | Delphia |
| 4,834,084 A | 5/1989 | Walsh |
| 5,020,530 A * | 6/1991 | Miller .................... 128/203.28 |
| 5,086,765 A | 2/1992 | Levine |
| 5,170,782 A | 12/1992 | Kocinski |
| 5,203,775 A * | 4/1993 | Frank et al. .................. 604/256 |
| 5,529,057 A | 6/1996 | Ferrero et al. |
| 5,685,291 A * | 11/1997 | Marsh .................... 128/200.15 |
| 6,176,234 B1 * | 1/2001 | Salter et al. ............ 128/200.18 |
| 6,182,655 B1 | 2/2001 | Keller et al. |

(Continued)

*Primary Examiner*—Steven O Douglas
*Assistant Examiner*—Kristen C Matter
(74) *Attorney, Agent, or Firm*—Dicke, Billig & Czaja, PLLC (57) ABSTRACT

A respiratory circuit inhalation apparatus is adapted to communicate a fluid stream between at least one air source and a patient and is formed with at least one central body portion defining an interior fluid stream communication passageway. An integrally formed dual function mouthpiece and effluent port projects from an end of the central body to communicate the fluid stream between the air source and a portion of the respiratory circuit that can lead to the patient or other components of the respiratory circuit. An integrally formed ambient fluid port is also formed as part of the inhalation apparatus that projects from the central body portion opposite to the dual function port. As with the other ports, the ambient fluid port also communicates the fluid stream between the interior fluid passageway and the at least one air source. The preferred inhalation apparatus also further includes a medication port that is formed about the central body portion and which includes a baffle or baffle portion that projects into and terminates within the interior fluid passageway. The terminus orifice and exit plane of the baffle preferably projects and terminates within the interior fluid passageway beyond the surface thereof so that liquids pooled within the passageway can be retained therein without draining into the medication port. Any or all of the various ports can be configured to be compatible for use with industry preferred respiratory circuit components and rigid and deformable 22 millimeter tubes.

28 Claims, 4 Drawing Sheets

U.S. PATENT DOCUMENTS 6,363,932 B1 4/2002 Forchione et al.
6,390,090 B1 5/2002 Piper
7,270,123 B2 * 9/2007 Grychowski et al. ... 128/200.14

* cited by examiner

INHALATION APPARATUS

TECHNICAL FIELD

This invention relates to the field of respiratory inhalation system mouthpieces and what are commonly referred to by those skilled in the art as "T-ports" (or "tee ports") that are used in various combinations with aerosol, gaseous, and airborne medication and inhalation medicament delivery systems. Such systems can include, for example and without limitation, components that are commonly referred to and known to those having skill in the relevant arts as nebulizers, aerosol dispensers, and metered dose inhalers. Such components and systems are often used in medical applications where various fluids, gases, and other forms of medications are delivered in an air stream that is communicated to an airway of a patient via the respiratory circuit of the inhalation apparatus and system.

BACKGROUND OF THE INVENTION

Many attempts have been made to devise new and improved devices for use with inhalers, aerosol dispensers, and nebulizers. However, there has long been and there remains a need to reduce the number of components needed to employ and use such devices effectively. Also, increased competition has created the need for devices that are less expensive to manufacture, which has in turn established the as yet unmet but long felt demand for inhalation devices that have a reduced number of parts and components and that can be produced at lower production costs with improved performance characteristics.

One attempt at improving the art is described in U.S. Pat. No. 4,007,238 to Glenn, which is limited to examples of a multi-part, complicated, and costly to fabricate nebulizer that incorporates multiple air passage ports and a mouthpiece. However, the Glenn nebulizer is restricted to a number of various components that must be fabricated and then assembled together. Additionally, each of the Glenn components incorporates a range of complex surface profiles and includes features that are challenging to form during fabrication, which complexities and challenges only serve to create further increases in part and fabrication costs, among other problems.

Another prior art attempt is set forth in U.S. Pat. No. 6,390,090 B1 to Piper, which is limited to an inhalation therapy device that is specially adapted for use with reservoir type bags that collapse and expand in response to patient respiration so as to store and reintroduce aerosolized gas as a patient inhales and exhales. Many different components are needed for the Piper '090 device to operate as intended. The Piper components include, among other limitations, a mouthpiece and various ports connected by air passageways that must be fabricated and assembled together in a complex and time-consuming manner to fashion the Piper device. As with other prior attempts, the Piper device suffers from unnecessarily complicated assemblies that increase difficulties to the user and practitioner and that also increase costs of production.

Forchione et al. in U.S. Pat. No. 6,363,932 B1 discloses yet another prior attempt to address some of the problems in the art of inhalation devices. Forchione et al. teach an aerosol enhancement device that incorporates a number of components akin to the configuration set forth by the Glenn '238 device that is described above. As with earlier attempts, the Forchione et al. device requires that numerous parts be formed and assembled together to establish the intended objective of communicating medicated air to a patient through a mouthpiece. What is missing from the prior art devices of record here and what continues to be needed is a device that is compatible for use with a wide range of nebulizers, inhalers, and dispensers and that is compatible with and that can be used in any number of possible air passage circuits that may be needed in various applications. The more desirable inhalation device would preferably simultaneously reduce manufacturing costs, decrease the number of parts needed to achieve the objective of communicating medicated air and gases to a patient, and that further reduces the attendant production and implementation costs while increasing operational efficiencies and performance characteristics. The present invention addresses these and other needs and overcomes many of the problems experienced with the prior art devices in a variety of new and novel configurations and with any of a number of possible and equally effective embodiments, configurations, and alternative and preferred and optional arrangements.

SUMMARY OF INVENTION

In its most general configuration, the present invention advances the state of the art of inhalation devices generally and T-ports and mouthpieces specifically with a number of innovative improvements and enhanced features and capabilities that advance the state of the art while reducing part counts and while increasing ease of use and operational efficiencies. The preferred respiratory circuit inhalation apparatus is adapted to be compatible with the wide array of existing respiratory circuit and inhalation apparatus components, tubes, and devices that are used in general for communicating a fluid stream between a patient and at least one controlled or ambient air source, such as a filtered, humidified, and/or oxygenated source. Additionally, the preferred device is adapted to further communicate medication from the at least one air source or additional such sources. More specifically, the preferred respiratory circuit inhalation apparatus incorporates, among other features and components, a central body portion that defines an interior fluid stream communication passageway. From an end of the central body portion, an integrally formed dual function effluent port or mouthpiece projects generally outwardly and communicates the fluid stream between the at least one air source and a mouth of the patient or another component or tube element of the respiratory circuit.

Projecting in an opposite direction from the dual function effluent port or mouthpiece is an ambient fluid port that is also adapted to communicate the fluid stream between the interior fluid passageway and the at least one air source and/or an ambient air source and/or other components of the contemplated respiratory circuit. The preferred inhalation apparatus also further incorporates at least one medication port that is formed about the central body portion and that is formed with a baffle or baffle portion that projects up and into the interior fluid passageway to limit or prevent any pooled liquids in the passageway from draining into the medication port.

In variations of the embodiments of the instant invention, the dual function effluent port and mouthpiece can be formed to have a profile that substantially conforms to a preferred patient mouth profile that can be adapted for infants, non-ambulatory individuals, children, adults, and others having specialized or special needs-type mouth breathing device requirements. Other configurations of the instant inhalation apparatus can be adapted to conform to variously desirable ASTM-type respiratory circuit component standards directed to diametrical dimensions and profiles. The medication port of the contemplated embodiments may be modified to be compatible for use with a variety of industry accepted components and devices that can include nebulizers, aerosol dispensers, metered dose inhalers, and similarly capable medication dispensing devices.

As those skilled and knowledgeable in the relevant and related arts may be able to further contemplate, the preferred and alternative configurations of the embodiments of the instant invention are also preferably or optionally adapted to incorporate a large number of possible additional alternative configurations and arrangements that are described in further detail herein below. These variations, modifications, and alterations of the various preferred and alternative embodiments and configurations may be used either alone or in combination with one another as can be better understood by those with skill in the art with reference to the following detailed description of the preferred and optional embodiments and the accompanying figures and drawings.

BRIEF DESCRIPTION OF THE DRAWINGS

Without limiting the scope of the present invention as claimed below and referring now to the drawings and figures, wherein like reference numerals, and like numerals with primes, if any, across the several drawings, figures, and views refer to identical, corresponding, and/or equivalent elements, components, features, and parts:

Also, in the various figures and drawings, reference symbols and letters are used to identify significant features, capabilities, dimensions, objects, and relative configurations and arrangements of elements as described in further detail herein below in connection with the several figures and illustrations.

DETAILED DESCRIPTION OF THE INVENTION

The preferable single piece construction and configuration of the respiratory circuit inhalation apparatus of the instant invention establishes a T-port that is less costly to manufacture and which eliminates the additional components and elements present in prior art devices. The inventive and novel inhalation apparatus described here is compatible for use in many inhalation therapies and protocols and can be implemented in conjunction with a variety of readily available respiratory related devices that can include, for purposes of example but not for purposes of limitation, nebulizers, aerosol dispensers, metered dose inhalers, and related medication dispensing devices, as well as humidified, oxygenated, filtered, and otherwise controlled air sources. The heretofore unavailable features and capabilities of the inhalation apparatus of the instant invention are now described in more detail in the context the preferred and optional embodiments as well as the desirable and optional modifications, alternatives, and variations thereof.

Figure 1:
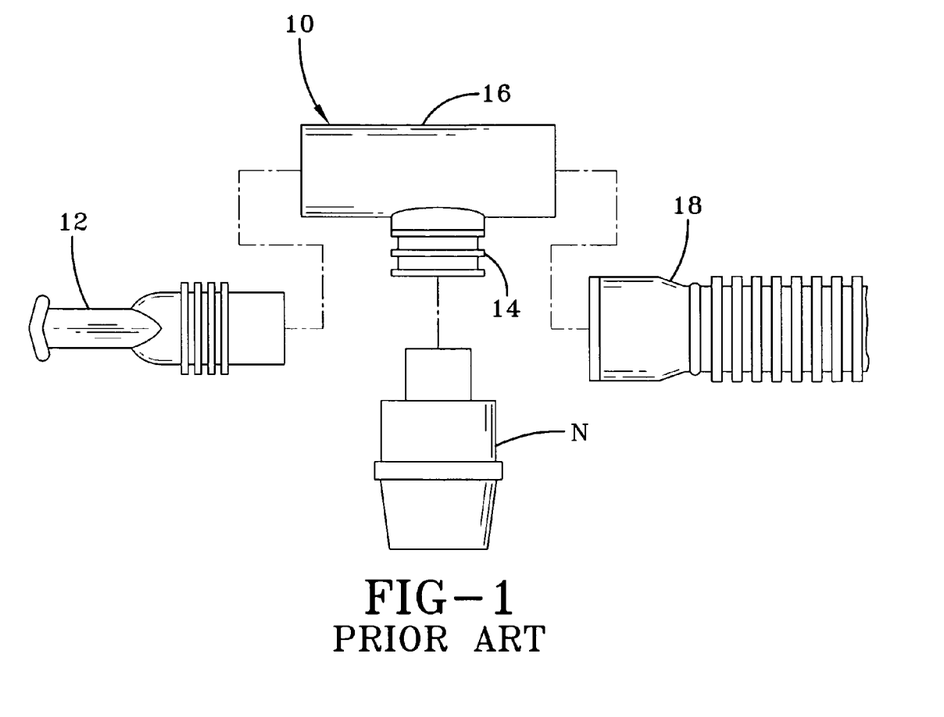
FIG. 1 is a side view, in modified scale, of an exemplary prior art T-port that shows the separate parts in a respiratory circuit with other components of an inhalation apparatus.
Figure 2:
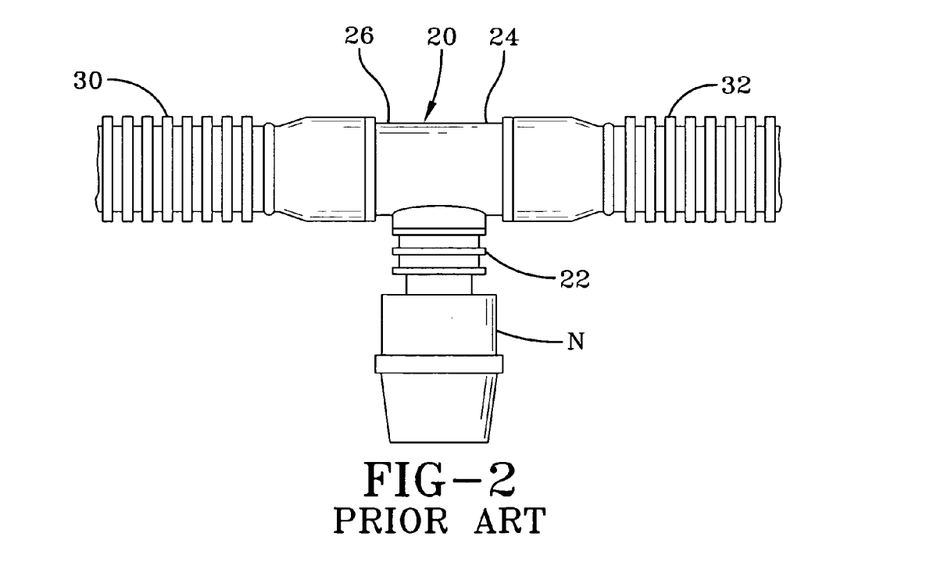
FIG. 2 is a side view, in modified scale, of another exemplary prior art T-port that has been assembled together in a respiratory circuit similar in configuration to that of FIG. 1.

With reference now to the various figures and specifically to FIGS. 1 and 2, various prior art devices that are formed from a number of separate parts that are molded separately are illustrated for purposes of comparison. In FIG. 1, there is depicted an inhaler 10 that includes a separate mouthpiece 12. The inhaler 10 has a downwardly projecting nebulizer port 14 that is connected to a nebulizer N. The inhaler 10 also incorporates a tubing port 16 that is connected to a tube 18 of a respiratory circuit. In another exemplary illustration of a prior art configuration of a respiratory circuit, in FIG. 2, a T-port 20 is shown that is received about a nebulizer port 22 with the nebulizer N, and about air stream ports 24, 26 with tubes 30, 32 of the respiratory circuit.

Figure 3:
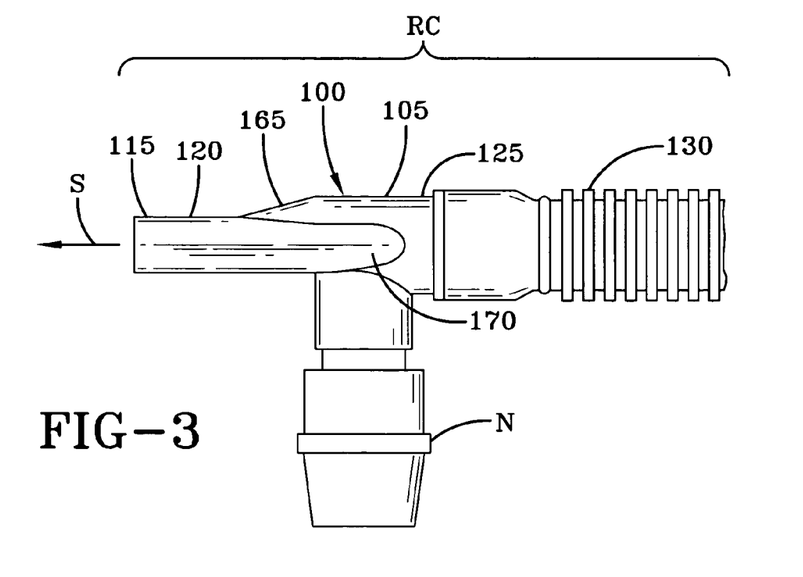
FIG. 3 is a side view, in modified scale, of a respiratory circuit that incorporates an inhalation apparatus according to the principles of the instant invention.
Figure 4:
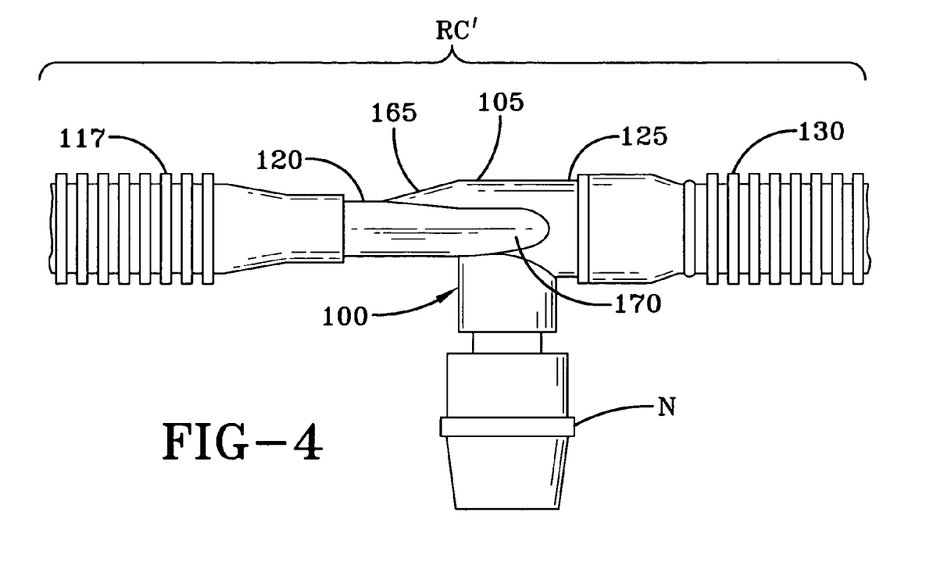
FIG. 4 is a side view, in modified scale, of an alternative respiratory circuit configuration of the inhalation apparatus of FIG. 3.
Figure 5:
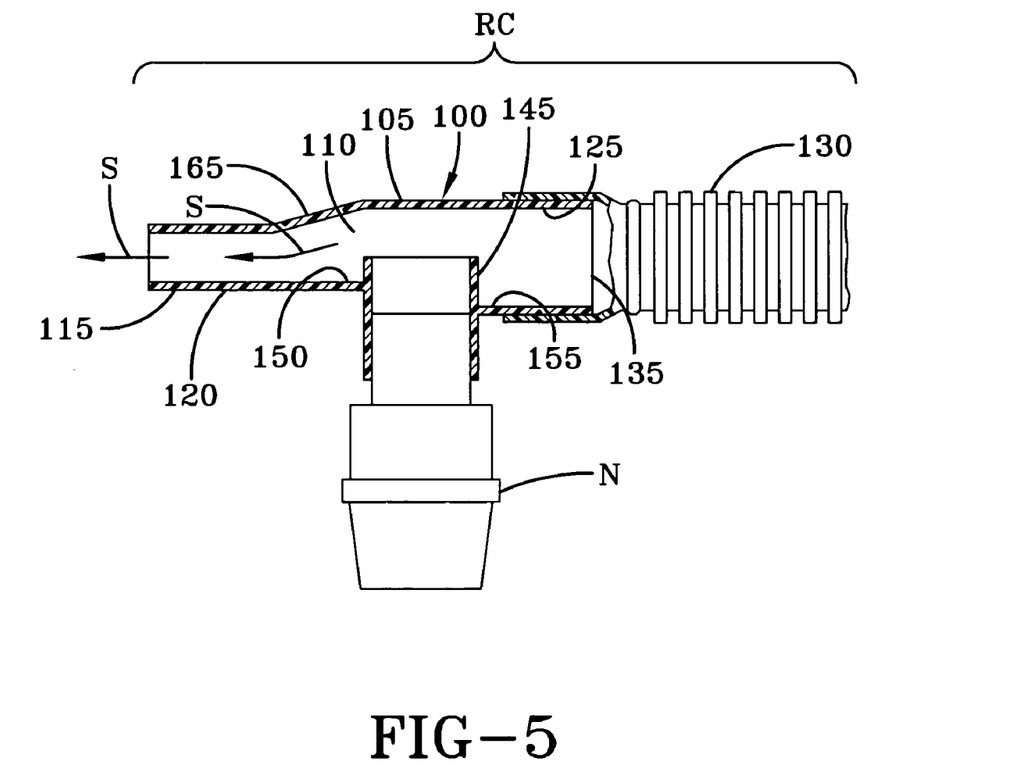
FIG. 5 is a breakaway detail view, in modified scale and with certain structure removed for purposes of illustration, of the respiratory circuit and inhalation apparatus of FIG. 3.
Figures 6, 8, 9:
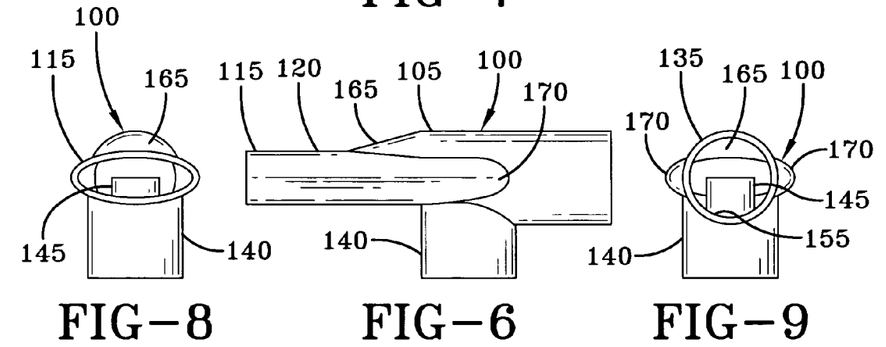
FIG. 6 is a side view, in modified scale, of the inhalation apparatus of FIGS. 3, 4, and 5, with certain structure of the respiratory circuit removed for further illustration purposes.
FIG. 8 is a side end view, in similar scale, of the inhalation apparatus of FIG. 6.
FIG. 9 is an opposite side end view, in similar scale, of the inhalation apparatus of FIG. 6.
Figure 7:
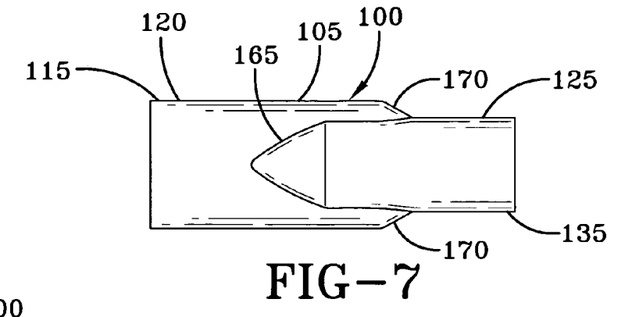
FIG. 7 is a topside view, in similar scale, of the inhalation apparatus of FIG. 6.
Figure 10:
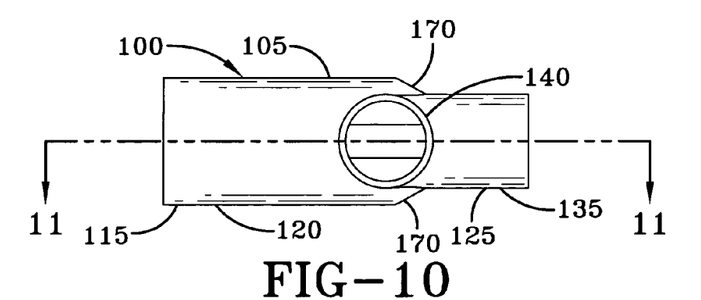
FIG. 10 is an underside side view, in similar scale, of the inhalation apparatus of FIG. 6.

With continued reference to the various figures and turning now also to FIGS. 3, 4, and 5, an inhalation apparatus 100 according to the principles of the instant invention is shown configured for use with respiratory circuits RC (FIG. 3) and RC' (FIG. 4) in mouth breathing inhalation therapy applications wherein a patient may use the apparatus 100 to inhale a controlled and/or medicated fluid and air stream S from at least one air source (not shown).

The inhalation apparatus 100 is formed with a central body portion 105, which is formed with an interior fluid passageway 110 (FIG. 5) that communicates the fluid stream S during respiration to and from the patient (not shown) and the air source. The preferred inhalation apparatus 100 is further formed with a dual function effluent port and/or mouthpiece 115 that extends or projects from an end 120 of the central body 105. As depicted in FIGS. 3 and 4, the dual function effluent port and/or mouthpiece 115 is preferably adapted to be received in or proximate to the mouth of the patient (FIG. 3) and/or can be connected to tubing 117 of the respiratory circuit RC' (FIG. 4) for communication either directly to the patient or to other respiratory circuit components.

For purposes of example without limitation, the dual function effluent port and/or mouthpiece 115 can be integrally formed with the central body 105 in any number of ways, including a single-shot type injection molding process. Also formed as part of and extending away from the central body 105 is an ambient fluid port 125, which projects away from the central body portion in a direction substantially opposite to the mouthpiece 115 and which communicates the fluid stream S between the interior fluid passageway 110 and the air source via tube 130 that can be connected to an end 135 of the ambient fluid port 125.

Each of the dual function effluent port and/or mouthpiece 115 and the ambient fluid port 125 are depicted in the various figures as being received, respectively, with tubes 117, 130 in a telescoping connection. Even so, many other equally effective connection methods can be employed to join the tubes 117, 130 to the ports 115, 125, and is described in further detail elsewhere herein. More specifically, in other optional or preferred configurations, the dual function effluent port and/or mouthpiece 115 and the ambient fluid port 125 are configured with a circumfluential cross-sectional terminus profile or periphery or peripheral edge that define an exit plane that is adapted to telescopically receive a deformable ASTM-type 22 millimeter respiratory circuit tube that can be similar in construction and capability to the tubes 117, 130.

A medication port 140 is also preferably formed with and about the central body portion 105 with a baffle or baffle portion 145 that terminates in an exit orifice that projects generally upward to extend generally into a central portion of the interior fluid stream communication passageway 110. Even more preferably, the baffle or baffle portion 145 extends therein a distance that is approximately between ⅓ and ½ of the average diameter or diametrical dimension of the interior fluid stream communication passageway 110.

In these configurations, the baffle or baffle portion 145 extends above a lower portion of the interior surfaces 150, 155 (FIG. 5) of the interior fluid stream communication passageway 110. As can be understood with continued reference to FIG. 5, the surfaces 150, 155 may be configured relative to one another whereby any liquid that is pooled thereon will, depending upon the orientation of the inhalation apparatus 100 as it is being held by the patient or user, flow generally from the surface 150 to the surface 155 and towards the ambient fluid port 125. In this way, liquids can be prevented from draining into the medication port 140, which limits contamination of the contents and surfaces of the medication dispensing device, such as nebulizer N. Additionally, the tube or tubing 130 that is connected to the ambient fluid port 125 can serve as or be replaced by a reservoir that can operate to capture any medication that may condense and pool in the inhalation apparatus 100 during use. The captured medication can then have an opportunity to evaporate and/or sublime back into air stream S, which further improves the likelihood that the patient will receive the full measure of the desired and/or prescribed medication.

The medication port 140 is also preferably configured to be connected to a medication dispensing or other equally desirable device or contemplated respiratory circuit component or tube, which medication dispensing devices can include nebulizers, such as nebulizer N, aerosol dispensers, and metered dose inhalers. Although the medication port 140 is shown in the various figures as being telescopically connected to the medication dispensing device, such as nebulizer N, many other equally suitable connection methods may be employed and can include, for purposes of example without limitation, threaded connections, twist-lock connectors, Luer-lock type connections, quick-release connections, and similarly capable connections and connectors.

With continued reference to the figures of the instant detailed description of the invention, and also now to FIGS. 6, 7, 8, 9, 10, and 11, those having skill in the art may also further be able to comprehend that the inhalation device 100 according to the principles of the instant invention may also be preferably or optionally formed to have a tapered region 165 that incorporates tapering nacelles 170, which are adjusted and configured to cooperatively graduate the interface of the central body portion 105 between the dual function effluent port and/or mouthpiece 115 and the ambient fluid port 125. This generally tapered region 165, 170 can be configured with greater or less overall and combined taper to minimize, for flow rates having generally low Reynolds numbers, turbulence of the fluid stream S as it passes through the fluid stream communication passageway 110.

Another benefit of the preferred or optional tapered region 165, 170 is that, under the ordinary inhalation therapy protocols, a venturi effect can be established during inhalation of the fluid stream S by the patient. This preferred or optional and possibly desirable venturi effect can be ensured by appropriate configuration and modification of the tapered region 165, 170 and the venturi capability will lower the ambient pressure proximate to and relative to that within the medication port 140, which in turn thereby operates to accelerate the inflow of medication aerosol from the medication port 140 and into the fluid stream communication passageway 110. Yet another tertiary benefit of the taper and/or tapered region 165, 170 is directed to manufacturing improvements wherein the injection molding components can be more efficiently designed so as to reduce the number of injection molding steps as well as the number of moving parts needed to form the inventive inhalation apparatus 100.

In the context of the contemplated venturi effect that is established by the tapered region or ramped area 165, 170, the inhalation apparatus 100 is preferably or optionally adapted wherein the cross-sectional area of the exit plane of the dual function effluent port and/or mouthpiece 115 is configured to be approximately less than the sum of the respective cross-sectional areas of the exit planes of the ambient fluid port 125 and the medication port 140. In this way, with the compressible and incompressible fluid flow principles of mass conservation in mind, those skilled in the relevant arts may come to understand that the fluid stream S will be necessarily accelerated as the patient inhales the air stream S and thereby induces the air stream S to move through the passageway 110 towards and across the tapered region or ramp 165, 170.

In one of many possible and desirable configurations of the inhalation apparatus 100 of the instant invention that have been found to be especially well-suited for a wide range of respiratory circuit inhalation therapeutic applications, the apparatus 100 was formed to have a substantially longitudinal dimension between the opposite outermost edges of the dual function effluent port and/or mouthpiece 115 and the ambient fluid port 125 of about 3 inches (approximately 76 millimeters). The dual function effluent port or mouthpiece 115 was selected to have a generally oval cross-sectional profile that substantially conforms to a preferred patient mouth profile and that had a minor diameter of approximately 0.5 inches (about 13 millimeters) and a major diameter of about 1.25 inches (about 32 millimeters). The ambient fluid port 125 and the medication port 140 were established to have similar generally cylindrical cross-sectional profiles with the ambient fluid port 125 having a diameter of about 0.87 inches (about 22 millimeters) and the medication port 140 having a diameter of about 0.83 inches (about 21 millimeters), which dimensions are compatible for use with many suitable respiratory circuit tubing, ASTM compatible air source, tubing, and medication dispensing devices.

Figure 11:
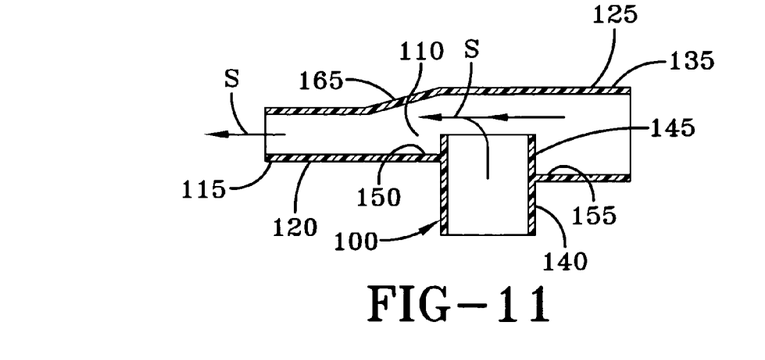
FIG. 11 is cross-sectional view, in similar scale and rotated and taken about section line 11-11, of the inhalation apparatus of FIG. 10.

The preferably or optionally centrally disposed baffle or baffle portion 145 was selected to extend to a substantially central position relative to the dimensions and configuration of the ambient fluid port 125 within the passageway 110 as can be best understood with reference to FIGS. 5 and 11. A dimension from the uppermost edge of the exit orifice of the baffle or baffle portion 145 to the lowermost edge of the medication port 140 was selected to be approximately 0.87 inches (or about 22 millimeters). With these relative dimensional constraints, the tapered region or ramp 165, 170 is then empirically varied to establish the most desirable Reynolds number and the most desired turbulent or laminar flow patterns based upon the anticipated and preferred performance characteristics needed for the particular inhalation therapy protocol. The additional variables considered included the anticipated or prescribed patient respiration rate range, the anticipated controlled air medium and medication to be inhaled or respired, the anticipated humidity, pressure, viscosity, and the like of the ambient air stream S that will be supplied by the at least one air source, and the related variables. One configuration of the taper region or ramp 165, 170 that was found to be particularly effective in accomplishing the most desirable performance characteristics in view the above, example dimensional constraints, included the taper being configured with a substantially longitudinal dimension of approximately 0.85 inches (about 21.5 millimeters) in the orientation shown generally in the various figures, most notably in FIGS. 3-7 and 11.

While one particular set of well-suited dimensional constraints has been described for purposes of illustration, the instant inventive inhalation apparatus 100 contemplates and is susceptible for larger and smaller scale uses and for a wide range of equally effective, and desirably and optionally different dimensional configurations, which can be adapted as needed for compatibility with a range of applications. Accordingly, the instant detailed description of the invention and the preferred and optional embodiments, and the modifications and alternatives thereof, are not intended to illustrate the only possible configurations but are instead aimed at enabling those having skill in the art to practice the invention in any of its most desired and optional configurations.

With respect to the various embodiments, configurations, modifications, and alternative arrangements set forth herein and otherwise contemplated by the apparatus 100 according to the principles of the instant invention, it has been unexpectedly discovered that, what those having skill in the relevant arts often refer to as pressure drops, head losses, and flow resistances are markedly improved in comparison to comparable configured prior art devices. More specifically, when compared to, for purposes of example but not for purposes of limitation, the multi-part, multi-component prior art devices illustrated in connection with FIGS. 1 and 2, the apparatus 100 has demonstrated much improved flow rates. For purposes of further comparison, explication, and illustration, but not for purposes of limitation, the instant inventive inhalation apparatus 100 in its many configurations and arrangements of elements, and the contemplated prior art devices, were exercised using various fluid flow rates through the apparatus 100 that were varied from approximately between 30 and 90 liters of gas per minute.

The pressure drop through the inventive devices 100 and the prior art devices were measured for various and specific flow rates for a variety of gases including room temperature ambient air and various inhalants and medicaments. As expected, the measured pressure drop through the inventive devices 100 and the prior art devices increased as the rate of flow was increased. However, unexpectedly, the pressure drop demonstrated by the inventive apparatus 100 was consistently found to be approximately between 68% and 72% less than the pressure drop exhibited by the multi-part, multi-component prior art devices. More particularly, the prior art devices demonstrated head losses of between about 1.9 to about 17 millimeters of $H_2O$ for flow rates of between about 30 and about 90 liters per minute of gas. In surprising contrast, the inventive apparatus 100 demonstrated only between about 0.6 and 5.1 millimeters of $H_2O$ of pressure drop through the apparatus 100 for comparable flow rates.

One or more of the components of the contemplated inventive inhalation apparatus 100 of the instant invention can be fabricated from a polymer material that is known to be compatible for use with the largest possible range of contemplated applications. Also, the preferred, optional, or desired material for the inhalation apparatus 100 can be selected for use in special purpose applications and environments as may be desirable or otherwise required. Such polymers that are preferred for purposes of the contemplated inhalation apparatuses contemplated and illustrated herein are most commonly selected from the group of materials that includes, for purposes of use with any of the preferred and alternative embodiments without limitation, glass, ceramics, metals, thermoset and elastomer monomers and polymers, and monomeric and polymeric thermoplastics including, for further purposes of illustration but not for purposes of limitation, elastomerics and thermoplastics selected from any of a variety of commercially available and suitable materials including acetyl resins, delrin, fluorocarbons, polyesters, polyester elastomers, metallocenes, polyamides, nylon, polyvinyl chloride, polybutadienes, silicone resins, ABS (acrylonitrile, butadiene, styrene), polypropylene, liquid crystal polymers, alloys and combinations and mixtures and composites thereof, and reinforced alloys and combinations and mixtures and composites thereof.

Many suppliers of such polymeric compounds are known and available and one such supplier includes Dow of Midland, Mich., USA, a manufacturer of virgin and recycled polymeric compounds. Such supplied polymers can differ from one another in their thermal, optical, and other properties and can be selected to accommodate a wide range of preferred characteristics as may be needed or desirable for particular applications of the preferred and optional embodiments of the inhalation apparatus 100 according to the instant invention. For purposes of further examples, the United States Department of Health and Human Services has, through the Food and Drug Administration, designated and identified various possibly suitable materials in Title 21 of the United States Code of Federal Regulations (CFR) Parts 170 through 199 and parts 800 through 1299, among other relevant sections of the CFR.

In addition to the various embodiments and configurations described herein, those skilled in the relevant arts can appreciate that the instant invention also further contemplates a number of other alterations, modifications, and variations that are all within the scope of the instant invention. All such alternative and modified embodiments are contemplated to be within the spirit and scope of the instant invention, which is intended to be limited only by the following claims. Although many specific embodiments and variations have been described herein in detail, those with skill in the art can and should comprehend and understand that the described embodiments and variations can be further modified to incorporate various types of substitute and/or additional materials, relative arrangements and alternative configurations of components, features, and elements. Moreover, such additional configurations can be also adapted with many possible dimensional configurations for compatibility with the wide variety of possible respiratory circuits and inhalation apparatus and components that are presently known in the art and that are in use in various fields, including medical, institutional, hospice, and residential environments. Accordingly, even though only few illustrative embodiments, alternatives, variations, and modifications of the instant invention are set forth herein, it is to be understood that the practice of such additional and alternatively preferable modifications and variations and the equivalents thereof, are intended to be within the spirit and scope of the invention as defined in the following claims.

We claim:

1. A respiratory circuit inhalation apparatus for communicating a fluid stream between at least one air source and a patient, comprising:

a central body portion that defines an interior fluid passageway that communicates the fluid stream;

a mouthpiece forming a mouthpiece opening and integrally formed with and projecting directly from an end of the central body and that communicates the fluid stream between a mouth of the patient and the at least one air source;

an integrally formed ambient fluid port with and projecting from the central body portion substantially opposite to the mouthpiece to communicate the fluid stream between the interior fluid passageway and the at least one air source; and a medication port formed about the central body portion having a baffle portion projecting into, and fluidly open within, the interior fluid passageway to define a baffle upstream side facing the mouthpiece and a baffle downstream side facing the ambient fluid port;

wherein the interior fluid passageway is fluidly open to an exterior of the apparatus only at the mouthpiece opening, the ambient fluid port and the medication port;

and further wherein the central body includes a narcelles region forming the fluid passageway to have an expanding dimension in extension toward the mouthpiece relative to a plane perpendicular to a central axis of the baffle portion such that the narcelles region defines a first maximum perpendicular dimension at a location aligned with the baffle downstream side and a second maximum perpendicular dimension at a location aligned with the baffle upstream side, the second maximum perpendicular dimension being greater than the first maximum perpendicular dimension;

and further wherein the inhalation apparatus maintains the second maximum perpendicular dimension in the plane perpendicular to the central axis from the location aligned with the baffle upstream side to the mouthpiece opening.

2. The respiratory circuit inhalation apparatus according to claim 1, wherein the mouthpiece is formed with a profile that substantially conforms to a preferred patient mouth profile.

3. The respiratory circuit inhalation apparatus according to claim 1, wherein the mouthpiece is formed with a profile that is defined to have a periphery adapted to telescopically receive a deformable ASTM-type 22 millimeter respiratory circuit tube.

4. The respiratory circuit inhalation apparatus according to claim 1, wherein the medication port is adapted to be telescopically connected to a medication dispenser selected from the group that includes a nebulizer, an aerosol dispenser, a medication source, and a metered dose inhaler.

5. The respiratory circuit inhalation apparatus according to claim 1, wherein the baffle portion is adapted with an exit orifice that projects into and terminates substantially centrally in the interior fluid passageway.

6. The respiratory circuit inhalation apparatus according to claim 1, wherein the baffle portion is adapted with an exit orifice that projects into and terminates in the interior fluid passageway a distance that is between approximately ⅓ and ½ of the average diameter of the interior fluid passageway.

7. The respiratory circuit inhalation apparatus according to claim 1, wherein the central body portion generally tapers in the direction of and to the mouthpiece, whereby an exit plane of the mouthpiece defines a cross-sectional area that is less than cross-sectional areas of respective exit planes of the ambient fluid and medication ports.

8. The respiratory circuit inhalation apparatus according to claim 7, wherein the central body portion has tapering nacelles.

9. The respiratory circuit inhalation apparatus according to claim 1, wherein the baffle portion projects through a floor of the central body and terminates at an end within the interior fluid passageway, the floor defined by an upstream side between the baffle portion and the mouthpiece and a downstream side between the baffle portion and the ambient fluid port, and further wherein a distance between the end of the baffle portion and the upstream side of the floor is less than a distance between the end of the baffle portion and the downstream side of the floor.

10. The respiratory circuit inhalation apparatus according to claim 1, wherein; the central body includes a tapered region spaced from the fluid port, the tapered region defining the interior fluid passageway to taper in a tapering dimension in extension toward the mouthpiece, the tapering dimension being parallel to the central axis.

11. The respiratory circuit inhalation apparatus according to claim 10, wherein the narcelles region is defined between the tapered region and the fluid port.

12. The respiratory circuit inhalation apparatus according to claim 10, wherein the tapering dimension is perpendicular to the expanding dimension.

13. The respiratory circuit inhalation apparatus according to claim 10, wherein the tapered region is entirely fluidly closed apart from the mouthpiece opening, a single opening formed by the ambient fluid port, and a single opening formed by the medication port.

14. The respiratory circuit inhalation apparatus according to claim 10, wherein expansion of the interior fluid passageway in the plane parallel to the central axis is symmetrical relative to a longitudinal central axis defined by the central body.

15. The respiratory circuit inhalation apparatus according to claim 1, wherein relative to a longitudinal cross-section, a floor of the apparatus is entirely uniformly linear from the baffle upstream side to the mouthpiece opening.

16. A respiratory circuit inhalation apparatus for communicating a fluid stream between at least one air source and a patient, comprising:

a central body portion that communicates the fluid stream through an interiorly defined fluid passageway;

an effluent piece integrally formed with and extending directly from an end of the central body and that communicates the fluid stream between the at least one air source and a portion of the respiratory circuit leading to the patient;

an integrally formed ambient fluid port with and projecting from the central body portion substantially opposite to the effluent piece and that is adapted to communicate the fluid stream between the interior fluid passageway and the at least one air source; and a medication port formed about the central body portion and having a baffle portion projecting into the interior fluid passageway and that is adapted with a baffle exit orifice that terminates in the interior fluid passageway, wherein relative to a longitudinal cross-section, a gap is established between the baffle exit orifice and an interior surface of the central body portion opposite the baffle exit orifice that is between approximately ⅔ and ½ of the average diameter of the interior fluid passageway;

wherein the interior fluid passageway generally tapers about the central body portion in the direction of and to the effluent piece and generally expands laterally out towards the sides of the central body portion at the baffle exit orifice as it extends to and forms part of the effluent piece.

17. The respiratory circuit inhalation apparatus according to claim 16, wherein the effluent piece is formed with a profile that substantially conforms to a preferred patient mouth profile and a predetermined ASTM-type profile of a deformable respiratory circuit tube.

18. The respiratory circuit inhalation apparatus according to claim 16, wherein the effluent piece is formed with a profile that is defined to have a periphery adapted to telescopically receive a deformable ASTM-type 22 millimeter respiratory circuit tube.

19. The respiratory circuit inhalation apparatus according to claim 9, wherein the medication port is adapted to be telescopically connected to a medication dispenser selected from the group that includes a nebulizer, an aerosol dispenser, a medication source, and a metered dose inhaler.

20. The respiratory circuit inhalation apparatus according to claim 16, wherein the exit orifice terminates substantially centrally in the interior fluid passageway.

21. The respiratory circuit inhalation apparatus according to claim 16, whereby an exit plane of the effluent piece defines a cross-sectional area that is less than the cross-sectional areas of respective exit planes of the ambient fluid and medication ports.

22. A respiratory circuit inhalation apparatus for communicating a fluid stream between at least one air source and a patient, comprising:
   a central body portion that defines an interior fluid passageway to communicate the fluid stream;
   a dual function port integrally formed with and extending directly from an end of the central body to communicate the fluid stream between the at least one air source and a portion of the respiratory circuit leading to the patient;
   an integrally formed ambient fluid port with and projecting from the central body portion substantially opposite to the dual function port and being adapted to communicate the fluid stream between the interior fluid passageway and the at least one air source; and
   a medication port formed about the central body portion and having a baffle portion projecting into the interior fluid passageway and terminating at a baffle exit orifice beyond the surface of the passageway, wherein relative to a longitudinal cross-section, an entirety of the baffle portion is linear;
   wherein the central body portion generally tapers in the direction of and to the dual function port and expands along the longitudinal cross-section in a region aligned with the baffle portion, wherein the central body portion has nacelles tapering in a direction opposite the dual function port.

23. The respiratory circuit inhalation apparatus according to claim 22, wherein the dual function port is formed with a profile that substantially conforms to a preferred patient mouth profile and a predetermined ASTM-type profile of a deformable respiratory circuit tube.

24. The respiratory circuit inhalation apparatus according to claim 22, wherein the dual function port is formed with a profile that is defined to have a periphery adapted to telescopically receive a deformable ASTM-type 22 millimeter respiratory circuit tube.

25. The respiratory circuit inhalation apparatus according to claim 22, wherein the medication port is adapted to be telescopically connected to medication dispenser selected from the group that includes a nebulizer, an aerosol dispenser, a medication source, and a metered dose inhaler.

26. The respiratory circuit inhalation apparatus according to claim 22, wherein the baffle portion is adapted with an exit orifice that projects into and terminates substantially centrally in the interior fluid passageway.

27. The respiratory circuit inhalation apparatus according to claim 22, wherein the baffle portion is adapted with an exit orifice that projects into and terminates in the interior fluid passageway a distance that is between approximately ⅓ and ½ of the average diameter of the interior fluid passageway.

28. The respiratory circuit inhalation apparatus according to claim 22, wherein the interior fluid passageway generally tapers about the central body portion in the direction of and to the dual function port, whereby an exit plane of the dual function port defines a cross-sectional area that is less than the sum of the cross-sectional areas of respective exit planes of the ambient fluid and medication ports.

* * * * *

UNITED STATES PATENT AND TRADEMARK OFFICE
CERTIFICATE OF CORRECTION

PATENT NO. : 7,721,734 B2  Page 1 of 1
APPLICATION NO. : 10/846415
DATED : May 25, 2010
INVENTOR(S) : Andre Rustad et al.

It is certified that error appears in the above-identified patent and that said Letters Patent is hereby corrected as shown below:

Column 5, line 3, delete "circumfluential," and insert -- circumferential --, therefor.

Column 7, line 57, delete "$H_20$" and insert -- $H_2O$ --, therefor.

Column 7, line 60, delete "$H_20$" and insert -- $H_2O$ --, therefor.

Column 10, line 12, in claim 10, delete "wherein;" and insert -- wherein --, therefor.

Column 11, line 12, in claim 19, delete "claim 9" and insert -- claim 16, --, therefor.

Signed and Sealed this

Thirteenth Day of July, 2010

David J. Kappos
*Director of the United States Patent and Trademark Office*